United States Patent [19]

Kleemann et al.

[11] 4,153,696

[45] May 8, 1979

[54] DIHYDROXYPHENYLETHYLAMINOAL-KYL THEOPHYLLINES

[75] Inventors: Axel Kleemann, Hanau; Karl H. Klingler, Langen; Ansgar von Schlichtegroll, Bad Homburg; Fritz Stroman, Offenbach; Klaus Thiemer, Hanau; Erik Westermann, Hannover-Buchholz, all of Fed. Rep. of Germany

[73] Assignee: Deutsche Gold- und Silber-Scheideanstalt vormals Roessler, Frankfurt, Fed. Rep. of Germany

[21] Appl. No.: 855,620

[22] Filed: Nov. 29, 1977

[30] Foreign Application Priority Data

Dec. 14, 1976 [GB] United Kingdom ............... 52071/76

[51] Int. Cl.$^2$ ............................................ C07D 473/08
[52] U.S. Cl. ..................................... 424/253; 544/272
[58] Field of Search ......................... 260/256; 424/253; 544/272

[56] References Cited

U.S. PATENT DOCUMENTS 3,398,150  8/1968  Klingler .................. 260/256
3,728,346  4/1973  Klingler .................. 260/256

FOREIGN PATENT DOCUMENTS 1221641  7/1966  Fed. Rep. of Germany.

*Primary Examiner*—Nicholas S. Rizzo
*Attorney, Agent, or Firm*—Cushman, Darby & Cushman

[57] ABSTRACT

There are prepared compounds of the formula

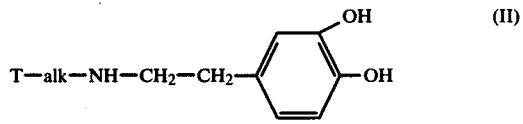

in which T is the theophyllin-7-yl group and alk is a straight or branched alkylene chain with 2 to 4 carbon atoms and salts thereof. The compounds promote circulation and produce a marked and persistent increase in renal circulation.

11 Claims, No Drawings

DIHYDROXYPHENYLETHYLAMINOALKYL THEOPHYLLINES

BACKGROUND OF THE INVENTION

This invention relates to new basically substituted theophylline derivatives.

Klingler German Patent Specification No. 1,221,641 described the production of theophylline derivatives corresponding to the general formula

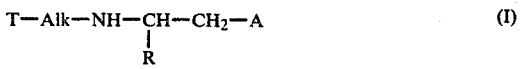

T—Alk—NH—CH—CH₂—A     (I)
              |
              R in which T represents theophylline radical, Alk represents a straight or branched alkylene chain with 2 to 6 carbon atoms, R represents a hydrogen atom or a lower alkyl group and A represents a phenyl radical which is substituted once, twice or three times by hydroxyl, methoxy, alkyl, aralkyl or alkoxy alkyl groups with 1 to 3 carbon atoms in the alkyl radical or by chlorine or bromine atoms or once by a methylene dioxy group in the 3,4-position.

These compounds are said to have a bronchospasmolytic effect and to stimulate cardiac circulation.

SUMMARY OF THE INVENTION

The present invention relates to basically substituted theophylline derivatives corresponding to the general formula

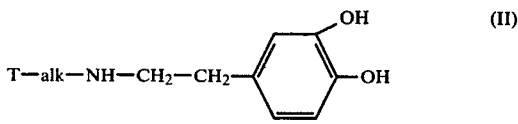

in which T represents the theophyllin-7-yl radical and alk is a straight or branched alkylene chain with 2 to 4 carbon atoms, and to their salts, more particularly their pharmaceutically acceptable salts.

It has been found that the compounds of formula (II) surprisingly promote circulation and, in particular, produce a marked and persistent increase in renal circulation. By contrast, the hitherto known compounds of general formula (I) have hardly any effect upon renal circulation.

The compounds according to the invention may be produced (a) by reacting a compound corresponding to the general formula

T—alk—X     (III)

in which T represents the theophyllin-7-yl radical and alk is an defined above, with a compound corresponding to the general formula

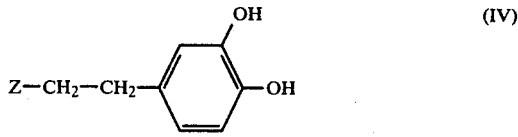

in which the hydroxy groups may be protected and in which X and Z are different and one represents a halogen atom and the other an optionally protected amino group, and splitting off any protective groups present in the compounds obtained, or (b) by subjecting a compound corresponding to the formula

T—alk'—W     (V)

to hydrogenating condensation with a compound corresponding to the formula

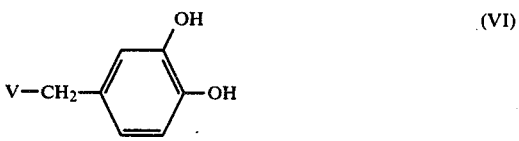

in which T is a theophyllin-7-yl radical and alk' represents a linear or branched alkylene chain with 1, 2 or 3 carbon atoms, W and V are different and either (1) W represents the group —CHR'—NH₂ and V the group —C(H)=O where R' represents a hydrogen atom or a methyl or ethyl group or (2) W represents the group —C(R')=O and V the group —CH₂—NH₂, and in which the hydroxy groups and the amino group may optionally be protected, and splitting off any protective groups present, or (c) in a compound of formula (II) in which T is the theophyllin-7-yl radical and alk is a linear or branched alkylene chain with 2 to 4 carbon atoms and in which the hydroxy groups and/or amino group are protected, by splitting off the protective groups present by hydrolysis and/or hydrogenation.

The compounds of general formula (II) may optionally be present in stereoisomeric or optically active forms and mixtures thereof, more especially in the form of racemates. Mixtures of diastereoisomers may be separated in known manner, for example by fractional crystallisation. Optically active compounds may be obtained by the usual methods, for example by recrystallising salts of the racemic bases of formula (II) with optically active acids or optionally by carrying out synthesis with optically active starting materials.

The end products of formula (II) are obtained either in free form or in the form of their salts, depending upon the process conditions applied and the starting materials used. The salts of the end products may be converted back into the bases in known manner, for example with alkali, e.g., sodium hydroxide or ion exchangers, i.e., anion exchangers. Salts can be obtained from the bases by reaction with organic or inorganic acids, especially those of the type which are capable of forming therapeutically acceptable salts. Examples of acids such as these are hydrohalic acids, e.g., hydrochloric acid or hydrobromic acid, sulphuric acid, phosphoric acid, phosphorous acid, nitric acid, perchloric acid, organic mono-, di- or tri-carboxylic acids of the aliphatic, alicyclic, aromatic or heterocyclic series and also sulphonic acids. Examples of these organic acids are formic acid, acetic acid, propionic acid, succinic acid, glycolic acid, lactic acid, malic acid, tartaric acid, citric acid, ascorbic acid, maleic acid, fumaric acid, hydroxy maleic acid or pyruvic acid; phenyl acetic acid, benzoic acid, p-aminobenzoic acid, anthranilic acid, p-hydroxy benzoic acid, salicyclic acid or p-aminosalicyclic acid, embonic acid, methane sulphonic acid, ethane sulphonic acid, hydroxy ethane sulphonic acid, ethylene sulphonic acid; halogen benzene sulphonic acids, e.g., p-chlorobenzene sulphonic acid, toluene sulphonic acid, naphthalene sulphonic acid or sulphanilic acid or even 8-chlorotheophylline.

In the methods described hereinafter for producing the compounds according to the invention, the amino groups entering into reaction and also the two phenolic hydroxy groups may contain known protective groups of the usual type. Protective groups such as these are radicals which may readily be split off by hydrolysis or hydrogenolysis and which, in many cases, are actually split off during the reaction itself. In cases where protective groups of the type in question are not split off during the reaction on which the process is based, they are split off after the reaction. In many cases, the starting compounds already contain protective groups of this type emanating from their production.

These protective groups are, for example, acyl groups which may readily be split off by solvolysis or groups which may be split off by hydrogenation. The protective groups capable of being split off by solvolysis are eliminated, for example, by hydrolysis with dilute acids or by means of basic substances (potash, soda, aqueous alkali solutions, alcoholic alkali solutions, NH$_3$) at temperatures of from 10° to 150° C. and more especially at temperatures of from 20° to 100° C. Groups which can be split off by hydrogenation, such as α-arylalkyl radicals (benzyl radical) or hydroxy carbonyl radicals (carbobenzoxy radical) are best eliminated by catalytic hydrogenation in the presence of standard hydrogenation catalysts, especially palladium catalysts, platinum oxide or even Raney nickel, in a solvent or suspending agent, optionally under elevated pressure, at temperatures in the range from 20° to 100° C. and more especially at temperatures in the range from 40° to 80° C. Suitable solvents and suspending agents are, for example, water, lower aliphatic alcohols, e.g., methanol, ethanol, isopropanol or butanol, cyclic ethers, such as dioxane or tetrahydrofuran, aliphatic ethers, e.g., diethyl ether or dipropyl ether, dimethyl formamide and the like, also mixtures thereof.

Examples of protective groups which may be split off by hydrogenolysis are the benzyl radical, the α-phenyl ethyl radical, benzyl radicals substituted in the benzene ring (the p-bromo- or p-nitrobenzyl radical), the carbobenzoxy radical, the carbobenzthio radical and the tert.-butyl hydroxy carbonyl radical. Examples of radicals which can be split off by hydrolysis are lower aliphatic acyl radicals, such as alkanoyl groups with 2 to 4 carbon atoms, e.g., the acetyl radical, propionyl radical or butyryl radical or the trifluoroacetyl radical, phthalyl radical, trityl radical, p-tolyl radical, p-toluene sulphonyl radical and the like, also the formyl radical, the tert.-butyl carboxy radical and the like.

Other protective groups for the phenolic hydroxy groups are lower alkoxy groups (1 to 6 carbon atoms), such as methoxy or ethoxy, also the methylene dioxy group. These ether groups are split off by hydrolysis in the presence of strong acids, e.g., hydrochloric acid or sulphuric acid.

The protective groups normally used in the synthesis of peptides and the techniques by which they are normally eliminated are particularly suitable. In this connection, reference is made inter alia to the book by Jesse P. Greenstein and Milton Winitz, entitled *Chemistry of Amino Acids*, New York 1961, John Wiley and Sons, Inc., Vol. 2, for example, pages 883 et seq. The carbalkoxy group (for example, low molecular weight) is also suitable.

Method (a) may be carried out in the absence of additional solvent or in the presence of a suitable solvent or dispersant. Examples of suitable solvents or dispersants are aromatic hydrocarbons such as, for example, benzene, toluene, xylene, mesitylene; ketones such as, for example, acetone, methyl ethyl ketone; halogenated hydrocarbons such as, for example, chloroform, carbon tetrachloride, chlorobenzene, methylene chloridel ethers such as, for example, tetrahydrofuran and dioxane; sulphoxides such as, for example, dimethyl sulphoxide; tertiary acid amides such as, for example, dimethyl formamide and N-methyl pyrrolidone; alcohols such as, for example, methanol, ethanol, isopropanol, amyl alcohol, tert.-butanol and so on. The reaction is carried out, for example, at temperatures of from 50° to 180° C. In cases where a solvent or dispersant is used, the reaction is frequently carried out at the reflux temperature thereof. In many cases, the reaction takes place at temperatures as low as normal temperature or at a temperature in the range from 20° to 50° C.

It can be of advantage to use the starting compound of general formula (III) in excess and/or to add the reaction component of general formula (IV) in dissolved or suspended form to the dissolved or suspended reaction component of general formula (III). The molar ratio between the compounds of general formulae (IV) and (III) may amount to between 1:1 and 1:10 or may even be higher.

The process is with advantage carried out in the presence of acid-binding agents, such as alkali metal carbonates, potash, soda, alkali metal hydroxides, e.g., sodium hydroxide, or tertiary bases. The amine component may optionally be used in excess.

In general, it is favourable for the two phenolic hydroxy groups of formula (IV) and also the amino group of one of the reactants of formula (III) or (IV) to be protected by protective groups of the type defined above. If these protective groups are not actually split off during the reaction itself, they may be removed on completion of the reaction in the manner already described.

Starting materials of formula (IV), in which Z is a halogen atom, may be obtained for example by reacting compounds of formula (IV), in which Z is a hydroxy group, with the corresponding hydrogen halide in accordance with Bodendorf in Liebigs Annalen der Chemie 563 (1949) 86–93.

Starting compounds of formula (IV), in which Z is the amino group, may be obtained, for example, from corresponding ω-nitro-3,4-dihydroxy styrene derivatives by reduction with LiAlH$_3$. Protective groups may be introduced into the phenolic hydroxy groups and the amino group by the method described in Borgman, Journal of Medicinal Chemistry 16 (1973) 630–633. The phenolic hydroxy groups may, of course, already be protected in the manner indicated in the ω-nitro-3,4-dihydroxy styrene and in the ω-halogen-3,4-dihydroxy ethyl benzene.

Method (b) may be carried out either at room temperature or at elevated temperature, e.g., from 20° to 150° C., and under normal pressure or elevated pressure, e.g., up to 50° C. The reactions on which this method is based are carried out in a solvent, such as alcohols, e.g., those set forth above, water-alcohol mixtures, dimethyl formamide or mixtures containing dimethyl formamide. The catalysts used are conventional hydrogenation catalysts, such as platinum, palladium or nickel with or without supports. In cases where protective groups capable of being split off by hydrogenolysis are present on the nitrogen of the side chain or on the hydroxyl groups of the phenyl radical, they are split off simultaneously, for example, in cases where palladium is used as the hydrogenation catalyst.

The reduction step may be carried out during condensation. Alternatively, the Schiff's base is first isolated and then reduced.

Starting compounds of formula (VI), in which (V) is an aminomethyl group, may be obtained for example from corresponding ω-nitro-3,4-dihydroxy styrene derivatives by reduction with LiAlH$_4$.

Starting compounds of formula (VI), in which (V) is the aldehyde group, may be obtained for example by splitting the corresponding glycols with lead tetraacetate (V=—CH(OH)—CH$_2$(OH)) (Houben-Weyl, Methoden der Organischen Chemie, Vol. 7/1, pages 352-356.

Protective groups may be introduced into the phenolic hydroxy groups and to the amino group by the method described in Journal of Medicinal Chemistry 16 (1973) 630–633. The phenolic hydroxy groups may, of course, already be protected in the manner indicated in the ω-nitro-3,4-dihydroxy styrene and in the (3,4-dihydroxy benzyl)-glycol.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical assistants, carriers and diluents.

Such carriers and assistants as set forth, for example, are those recommended in the following literature as adjuvants for pharmacy, cosmetic and related fields such as in Ullmann's Encyklopädie der technischer Chemie, Vol. 4 (1953), pages 1 to 39; Journal of Pharmaceutical Sciences 52 (1963), pages 918 et seq.; H. v. Czetsch-Lindenwald, Hilftstoffe für Pharmazie und angrenzenda Gebiete; Pharm. Ind. 2 (1961), pages 72 et seq.; Dr. H. P. Fiedler, Lexicon der Hilfstoffe für Pharmazie, Kosmetik und angrenzende Gebiete, Cantor Kg. Aulendorf i. Wurtt (1971).

Examples of such materials include gelatin, natural sugars such as sucrose or lactose, lecithin, pectin, starch (for example corn starch), alginic acid, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono-, di- and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acid (2 to 22 carbon atoms, especially 10 to 18 carbon atoms), with monohydric aliphativ alcohols (1 to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulphoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of gylcerine, e.g., monoacetic, diacetin, glyceryl monostearate, glyceryl distearate, glyceryl monopalmitate, paraffins and the like.

In the production of the preparations there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxylethylated sorbitan monooleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerisation generally is between 2 and 40, particularly between 10 and 20.

Such polyoxylethylated materials for example can be obtained by reaction of hydroxyl group containing compounds (for example, mono- or diglycerides or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, colloidal aluminium hydroxide, taste correctives, antioxidants and complex formers (for example, ethylene diamine tetracetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example, lower alkyl esters such as the methyl ester and the ethyl ester) benzoic acid, sodium benzoate, trichloroisobutyl alochol, phenol, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example, by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, pulmonarily, rectally, nasally, vaginally, lingually, intravenously, intraarterially, intracardially, intramuscularly, intraperitoneally, intracutaneously or subcutaneously.

It is also possible or desirable to add other medicinally active materials. The compounds of the invention show a good circulatory stimulating effect on complete animals in narcosis with electronic measurement of pressure and blood flow.

For example, there is produced with the above-mentioned test methods at a dosage of 0.003 mg per kg of body weight (in dogs) an increase in contractility of the left ventricle of about 66%.

The mimetic activity is comparable to the activity of the known medicine Dopamine.

The lowest clearly positive inotropically effective dosage in the above-mentioned animal experiments was for example 0.1 mg/kg body weight orally; 0.03 mg/kg sublingually, and 0.001 mg/kg intraveneously.

As the general dosage range for the positive inotropic activity (based on animal tests such as above) there can be used for example 0.1-10 mg/kg orally, particularly 3 mg/kg; 0.003-0.1 mg/kg intravenously, particularly 0.03 mg/kg.

The compounds of the invention are indicated for use in circulatory insufficiency (shock) of different genesis, chronic heart and renal insufficiency, symptomatic therapy with poisons.

The pharmaceutical preparations generally contain between 0.1 to 50 mg of the active component or components of the invention.

The compounds can be delivered in the form of tablets, capsules, pills, dragees, plugs, salves, gels, creams, powders, dusts, aerosols or in liquid form. As liquid forms there can be used for example oily or alcoholic or aqueous solutions as well as suspensions and emulsions. The preferred forms of use are tablets which contain between 0.1-5% of active material.

In individual doses the amount of active component of the invention can be used for example in an amount of:
 a. in oral dispensation between 10 and 300 mg;
 b. in parenteral dispensation (for example intravenously, intramuscularly) between 0.1 and 8 mg.
(The dosages in each case are based on the free base.)

For example, there is recommended the use of 1 to 3 tablets containing 10 to 150 mg of active ingredient 3 times daily or for example, intravenously the injection 1 to 6 times daily of a 1 to 10 ml ampoule containing 1 to 50 mg of active substance. In oral preparations the minimum daily dosage for example is 50 mg; the maximum daily dosage in oral administration should not be over 10 grams.

In veterinary medicine the compounds of the invention can be used in treating dogs and cats. The individual dosages in general are between approximately 0.3-10 mg/kg body weight; the parental dosages approximately between 0.03 and 0.3 mg/kg body weight orally.

For the treatment of horses and cattle the individual dosages orally is in general between about 0.5 and 20 mg/kg of body weight.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is between 150 mg/kg and 500 mg/kg, in some cases even above 1000 mg/kg.

The drugs can be used in human medicine, in veterinary medicine as well as in agriculture alone or in admixture with other pharmacologically active materials.

DESCRIPTION OF THE PREFERRED EMBODIMENTS

The invention is illustrated by the following examples:

EXAMPLE 1

7-{2-[2-(3,4-Dihydroxyphenyl)-ethylamino]-ethyl}-theophylline

A mixture of 14.0 g of 3,4-dibenzyloxy phenethylamine, 10.0 g of 7-(2-bromoethyl)-theophylline, 4.92 g of potassium carbonate and 20 ml of xylene is boiled under reflux with stirring for 7 hours. 70 ml of water are then added and the mixture stirred until the inorganic salts have dissolved. The xylene phase is separated off and concentrated by evaporation in vacuo. The residue is dissolved in acetone, precipitated with alcoholic hydrochloric acid and the 3,4-dibenzylated intermediate product is hydrogenated (optionally after recrystallisation from methanol) at 60° C. in a mixture of 600 ml of ethanol and 200 ml of methanol in the presence of 1 g of palladium carbon (5%). When hydrogen stops being taken up, the reaction mixture is filtered, concentrated by evaporation under nitrogen and purified by boiling with ethanol. 7.3 g of the above-mentioned compound in the form of its hydrochloride are obtained. M.P. of the hydrochloride: 239° C.

Instead of 14.0 g of 3,4-dibenzyloxy phenethylamine, 7.6 g of 3,4-dimethoxy phenethylamine for example may also be used for the reaction. In the intermediate product obtained in this case, namely, 7-{2-[2-(3,4-dimethyloxyphenyl)-ethylamino]-ethyl}-theophylline, the two protective methoxy groups are split off as follows: 1.4 g of the intermediate compound are boiled under reflux for 5 hours in 38 ml of acetic acid and 15 ml of 48% hydrobromic acid. After distillation in vacuo, the residue is recrystallised from ethanol, giving 0.9 g of the hydrobromide of the compound mentioned in Example 1. M.P. of the hydrobromide: 246° C.

EXAMPLE 2

7-{3-[2-(3,4-Dihydroxyphenyl)-ethylamino]-propyl}-theophylline

A mixture of 7.3 g of N-benzyl-2-(3,4-dibenzyloxyphenyl)-ethylamine, 5.6 g of 7-(3-iodopropyl)-theophylline, 2.25 g of potassium carbonate, 20 ml of toluene and 0.5 ml of water is boiled under reflux with stirring for 10 hours. The mixture is then diluted with 80 ml of toluene and extracted by shaking with 30 ml of water. The toluene phase dried with potassium carbonate is concentrated by evaporation in vacuo and the residue is dissolved in acetone. Acidification with alcoholic hydrochloric acid precipitates the hydrochloride of N-benzyl-7-{3-[2-(3,4-dibenzyloxyphenyl)-ethylamino]-propyl}-theophylline (9.2 g). This intermediate stage may be recrystallised from 90% isopropanol or may be directly hydrogenated at 60° C. in 440 ml of 90% ethanol in the presence of 2.4 g of palladium carbon (10%). After filtration, the reaction mixture is concentrated by evaporation in vacuo and the residue is recrystallised from methanol.

Yield: 4.5 g, M.P. of the hydrochloride 273° C.

EXAMPLE 3

7-{3-[2-(3,4-Dihydroxyphenyl)-ethylamino]-butyl}-theophylline

This compound is produced as in Example 1 by reacting 33.4 g of 3,4-dibenzyloxy phenethylamine with 24.0 g of 7-(3-bromobutyl)-theophylline in solution in toluene in the presence of 10.6 g of potassium carbonate and subsequently hydrogenating the dibenzylated intermediate stage with 1.5 g of palladium carbon (5%) in 200 ml of 90% ethanol at 60° C. The product is purified by boiling with absolute ethanol.

Yield: 15.2 g, M.P. of the hydrochloride 258°–260° C.

EXAMPLE 4

7-{2-[2-(3,4-Dihydroxyphenyl)-ethylamino]-ethyl}-theophylline 13 g of 7-{2-[2-(3,4-dibenzyloxyphenyl)-ethylamino]-ethyl}-theophylline hydrochloride (M.P. 180° C.) are hydrogenated at 60° C. in a mixture of 600 ml of ethanol and 200 ml of methanol in the presence of 1 g of 5% palladium carbon catalyst. After hydrogen stops being taken up, the reaction mixture is filtered, concentrated by evaporation under nitrogen and purified by boiling with ethanol. 7.3 g of the above-mentioned compound in the form of its hydrochloride are obtained. M.P. of the hydrochloride: 239° C.

EXAMPLE 5

7-{3-[2-(3,4-Dihydroxyphenyl)-ethylamino]-propyl}-theophylline 4.8 g of N-benzyl-7-{3-[2-(3,4-dibenzyloxyphenyl)-ethylamino]-propyl}-theophylline hydrochloride (M.P. 188°–190° C.) are hydrogenated at 60° C. in 220 ml of 90% ethanol in the presence of 1.2 g of a 10% palladium carbon catalyst. The reaction mixture is filtered, concentrated by evaporation in vacuo and recrystallised from methanol.

Yield: 2.3 g, M.P.: 273° C. (hydrochloride).

EXAMPLE 6

7-{3[2-(3,4-Dihydroxyphenyl)-ethylamino]-butyl}-theophylline

This compound is produced by hydrogenating 15 g of N-benzyl-7-{3-[2-(3,4-dibenzyloxyphenyl)-ethylamino]-butyl}-theophylline hydrochloride (M.P. 154° C.) in 70 ml of 90% ethanol at 60° C. in the presence of 1 g of palladium carbon (5%). After hydrogen stops being taken up, the reaction mixture is filtered, concentrated by evaporation under nitrogen and the residue is boiled with absolute ethanol.

Yield: 5 g, M.P.: 258°–260° C. (hydrochloride).

Examples of pharmaceutical formulations of the compound of Example 1 are given below:

Injection Solution 2 mg of the compound of Example 1 in the form of the hydrochloride salt was dissolved in 200 mg of propylene glycol and the solution filled up with water to a total volume of 2 ml. After filtration, the solution is filled into ampoules.

Tablets:

| A 150 mg tablet contained | |
|---|---|
| Compound of Example 1 | 50.0 mg |
| Lactose | 79.1 mg |
| Polyvinylpyrrolidone | 5.0 mg |
| Cornstarch | 15.0 mg |
| Highly dispersed silica | 0.5 mg |
| Magnesium stearate | 0.4 mg |

The compound of Example 1 was fixed with the lactose and cornstarch and moistened with a solution of polyvinyl pyrrolidone in water; the composition was thoroughly worked, dried, sieved and after addition of the highly dispersed silica and magnesium stearate pressed into tablets.

The compositions can comprise, consist essentially of or consist of the materials set forth.

What is claimed is:

1. A compound corresponding to the general formula

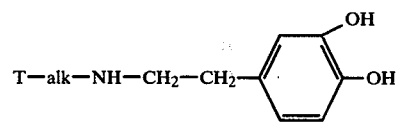

in which T is the theophyllin-7-yl radical and alk is an alkylene chain with 3 carbon atoms, or a pharmaceutically acceptable salt thereof.

2. A compound according to claim 1 in the form of the free base.

3. A compound according to claim 1 in the form of a pharmaceutically acceptable salt.

4. A method of increasing renal circulation in a mammal comprising administering to the mammal an effective amount to increase renal circulation of a compound corresponding to the general formula

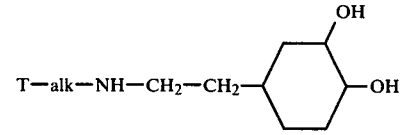

in which T is the theophyllin-7-yl radical and alk is an alkylene chain with 2 to 4 carbon atoms, or a pharmaceutically acceptable salt thereof.

5. A method according to claim 4 wherein the compound is 7-{3-[3,4,-dihydroxyphenyl)-ethylamino]-propyl}-theophylline.

6. A method according to claim 4 wherein alk is

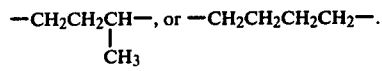

7. A method according to claim 6 wherein the compound is 7-{2-[2-(3,4-dihydroxyphenyl)-ethylamino]-ethyl}-theophylline.

8. A compound according to claim 6 which is 7-{3-[2-(3,4-dihydroxyphenyl)-ethylamino]-propyl}-theophylline.

9. A method according to claim 6 wherein the compound is 7-{3-[2-(3,4-dihydroxyphenyl)-ethylamino]-butyl}-theophylline.

10. A method according to claim 4 wherein there is administered orally at least 0.1 mg/kg body weight of the mammal.

11. A method according to claim 4 wherein there is administered intravenously at least 0.001 mg/kg body weight of the mammal.

* * * * *